United States Patent [19]

Lee et al.

[11] Patent Number: 5,714,135
[45] Date of Patent: Feb. 3, 1998

[54] HAIR TREATMENT COMPOSTION

[75] Inventors: G. Jae Lee, Trumbull; Susan Kay Hentrich, Fairfield, both of Conn.

[73] Assignee: Chesebrough-Pond's USA Co., Division of Conopco, Inc., Greenwich, Conn.

[21] Appl. No.: 616,953

[22] Filed: Mar. 18, 1996

[51] Int. Cl.$^6$ .................. A61K 7/06; A61K 7/11
[52] U.S. Cl. .................. 424/70.11; 424/70.31; 424/DIG. 2
[58] Field of Search .................. 424/70.11, 70.31, 424/DIG. 2

[56] References Cited

U.S. PATENT DOCUMENTS

| | | |
|---|---|---|
| 4,315,910 | 2/1982 | Nowak, Jr. et al. . |
| 4,983,377 | 1/1991 | Murphy et al. . |
| 4,983,383 | 1/1991 | Maksimoski et al. . |
| 5,034,220 | 7/1991 | Helloff et al. . |
| 5,034,486 | 7/1991 | Tzai et al. . |
| 5,066,481 | 11/1991 | Helloff et al. . |
| 5,266,308 | 11/1993 | Lee et al. . |

FOREIGN PATENT DOCUMENTS

| | | |
|---|---|---|
| 0 584 877 | 3/1994 | European Pat. Off. . |
| 0 617 954 | 10/1994 | European Pat. Off. . |
| 0 686 386 | 12/1995 | European Pat. Off. . |
| 92/02205 | 2/1992 | WIPO . |
| WO96/03967 A1 | 7/1994 | WIPO . |
| 94/26235 | 11/1994 | WIPO . |
| WO95/13788 | 5/1995 | WIPO . |

OTHER PUBLICATIONS

Research Disclosure vol. 33, No. 1, 1992, pp. 879–887; Decadiene Crosspolymer: A New Thickener/Stabilizer, pp. 883–884.

"Stabileze® Thickeners and Stabilizers", ISP Product Brochure 1995.

Cosmetics & Toiletries Mfg. Woldwide, Jan. 1996, Gripp et al.

Primary Examiner—Sally Gardner-Lane
Attorney, Agent, or Firm—Milton L. Honig

[57] ABSTRACT

A hair treatment composition for use with spray dispensers is provided which includes a crosslinked $C_1$–$C_{10}$ alkyl vinyl ether/maleic anhydride copolymer, a nonionic, surfactant and a film-forming resin. Preferably the compositions are transparent gels. They exhibit reduced clogging of spray nozzle pumps and provide excellent sensory properties.

6 Claims, No Drawings

HAIR TREATMENT COMPOSTION

BACKGROUND OF THE INVENTION

1. Field of the Invention

The invention relates to a hair styling composition, especially a sprayable gel dispensed through a pump mechanism.

2. The Related Art

Hairspays are products containing a film-forming resin which when applied to hair helps to hold the hair in place. Resins can be sprayed onto the hair utilizing different types of dispensers. Two of the most popular are the mechanical air driven pump container and the aerosol canister, the latter employing a volatile propellant to discharge product. Both types of dispensers include a spray nozzle through which product is sprayed.

Clogging of nozzle orifices is a perennial problem. Most often clogging is encountered with relatively viscous formulations, frequently the result of thickeners settling within the exit orifices. Carbomers which are the thickeners of choice in commercial products have especially been linked to plugging of orifices.

U.S. Pat. No. 4,983,377 (Murphy et al.) describes the use of silicone gums as highly effective conditioning and style retention aids. However, materials of this type may have deficiencies with respect to clogging. Improved materials are therefore necessary which can combine thickening, conditioning and style retention while still allowing for good sprayability.

Accordingly, it is an object of the present invention to provide a hair treatment composition suitable for dispensing through a pump without causing clogging of nozzles.

Another object of the present invention is to provide a hair treatment composition suitable for dispensing through a pump that not only provides excellent spray characteristics but also delivers excellent sensory properties.

Still another object of the present invention is to provide a hair treatment composition in the form of a clear gel with the properties of good sprayability, good styling and minimal tackiness.

These and other objects of the present invention will become more apparent from the detailed description which follows.

SUMMARY OF THE INVENTION

A hair treatment composition is provided including:

(i) from 0.01 to 10% by weight of a crosslinked $C_1$–$C_{10}$ alkyl vinyl ether/maleic anhydride copolymer;

(ii) from 0.1 to 20% by weight of a film-forming resin; and (iii) from 0.01 to 10% by weight of a nonionic surfactant.

DETAILED DESCRIPTION OF THE INVENTION

Now it has been discovered that a crosslinked alkyl vinyl ether/maleic anhydride copolymer in conjunction with a nonionic surfactant can deliver a film-forming polymer in aqueous solution as a uniform continuous spray. Clogging of pump nozzle orifices is no longer a significant problem. Moreover, these compositions deliver excellent sensory properties including conditioning, styling and luster.

A first essential element of the present invention is a crosslinked $C_1$–$C_{10}$ alkyl vinyl ether/maleic anhydride copolymer to serve as a thickening agent for the hair treatment composition. Most preferred is methyl vinyl ether/maleic anhydride copolymer crosslinked with 1,9-decadiene, commercially available as Stabileze QM® from ISP Corporation, Wayne, N.J. Particle size of the copolymer in powder form is preferably less than 100 micron. Amounts of the copolymer may range from 0.01 to 10%, preferably from 0.1 to 2%, optimally from 0.15 to 0.5% by weight.

The maleic anhydride segment of copolymers of this invention are preferably at least partially neutralized with base so that the copolymer becomes anionic. Suitable bases include sodium hydroxide, potassium hydroxide, ammonium hydroxide, triethanolamine, aminomethyl propanol, aminomethyl propanediol, tromethamine and tetrahydroxypropylethylenediamine. Amounts of the base relative to copolymer may range from 0.5:1 to 3:1.

A second essential element of the present invention is a nonionic surfactant. Generally this will be an ethoxylated or propoxylated adduct of a hydrophobe such as a $C_8$–$C_{22}$ fatty alcohol, $C_8$–$C_{22}$ fatty acid, $C_8$–$C_{22}$ fatty amine, $C_8$–$C_{15}$ alkylphenol, $C_{12}$–$C_{18}$ fatty acid sorbitan esters and $C_{12}$–$C_{18}$ fatty acid mono- and diglycerides. The amount of ethylene oxide or propylene oxide per mole of hydrophobe may range from 1 to 50 moles. More particularly the range of alkoxylation may range from 12 to 40 moles ethylene oxide or propylene oxide, most preferably from 20 to 30 moles. Particularly preferred are the ethoxylated nonionics, especially ethoxylated $C_8$–$C_{22}$ fatty alcohols. Quite effective are the $C_{18}$–$C_{22}$ fatty alcohols ethoxylated with from 20 to 30 moles ethylene oxide. Illustrative is polyethylene glycol 20-stearyl ether, known in CTFA nomenclature as Steareth-20, available commercially as Arosurf 66E-20.

A third essential element of the present invention is a water soluble film-forming resin. The resin may either be anionic, nonionic, amphoteric or cationic. Specific resins include polyvinylpyrrolidone (PVP), copolymers of (PVP) and methylmethacrylate, copolymers of PVP and vinyl acetate (VA), polyvinyl alcohol (PVA), copolymers of PVA and crotonic acid, copolymers of PVA and maleic anhydride, hydroxypropyl cellulose, hydroxypropyl guar gum, sodium polystyrene sulfonate, PVP/ethylmethacrylate/methacrylic acid terpolymer, vinyl acetate/crotonic acid/vinyl neodecanoate copolymer, octylacrylamide/acrylates copolymer, monoethyl ester of poly(methyl vinyl ether/maleic acid), and octylacrylamide/acrylate/butylaminoethyl methacrylate copolymers. Mixtures of resins may also be used. PVP and PVP copolymers with other monomers are preferred. The most preferred resins for use in the present hairsprays are copolymers of polyvinyl pyrrolidone and vinyl acetate, particularly a 70/30 ratio.

Amounts of the film-forming resin may range from 0.1 to 20%, preferably from 1 to 10%, optimally from 2 to 5% by weight.

Water will be present in compositions of the present invention. Amounts may range from 50 to 99%, preferably from 85 to 96% by weight.

Compositions of the present invention may be formulated as transparent or opaque emulsions, lotions, creams, pastes, mousses or gels. A particularly preferred form is that of a transparent gel having a viscosity sufficiently mobile for dispensing through a spray nozzle of a pump.

Compositions of the present invention will exhibit a pH ranging from 4.0 to 6.0, most preferably from 4.5 to 5.3.

Compositions of this invention advantageously can include hair conditioning agents. These agents may be selected from silicone compounds, quaternary ammonium polymers, phytantriol and mixtures thereof. Phytantriol is particularly useful because it not only conditions but adds stylability to hair-care compositions. Phytantriol as known by its CTFA name is a hydrophobic branched triol chemically identified as 3,7,11,15-tetramethyl-1,2,3-hexadecanetriol. Commercially it is available from Hoffmann-La Roche, Inc., Nutley, N.J. For purposes of the present invention, the amount of phytantriol will range from 0.0001 to 1%, preferably from 0.001 to 0.5%, optimally from 0.005 to 0.2% by weight.

Silicone compounds may be chosen from volatile and non-volatile silicone fluids. Volatile silicone fluids are preferably oils chosen from cyclic or linear polydimethyl siloxanes containing from 3 to 9, preferably from 4 to 5 silicon atoms.

Cyclomethicone is the most preferred cyclic volatile silicone. Linear volatile silicone oils generally have viscosities less than about 5 centistokes at 25° C. while cyclic fluids typically have viscosities of less than about 10 centistokes.

Nonvolatile silicone oils useful for the present invention include polyalkyl siloxanes, polyalkylaryl siloxanes and polyether siloxane copolymers. Non-volatile polyalkyl siloxanes useful herein include, for example, polydimethyl siloxanes with viscosities of from 5 to 100,000 centistokes at 25° C. Among the preferred non-volatile silicones are the polydimethyl siloxanes having viscosities from 10 to 400 centistokes at 25° C. These siloxanes are available, for example, from the General Electric Company as SF 1075 methyl phenyl fluid or from Dow Corning as 556 Cosmetic Grade Fluid.

The non-volatile polyalkylaryl siloxane fluids that may be used include, for example, polymethylphenylsiloxanes having viscosities of about 15 to 30,000 centistokes at 25° C. Extremely high molecular weight silicones known as silicone gums ordinarily will not be employed in compositions of this invention.

Among the quaternary ammonium polymeric conditioners, the most useful are the cationic guar gums. The CTFA name for a preferred guar gum is guar hydroxypropyltrimonium chloride. This material is available from Rhone-Poulenc under the trademark Jaguar®. Illustrative is Jaguar® C13S, having a low degree of substitution of cationic groups and a high viscosity. Other suitable varieties are Jaguar® C15, having a moderate degree of substitution and a low viscosity; Jaguar® C17 having a high degree of substitution and a high viscosity; and Jaguar® C16 which is a hydroxypropylated cationic guar derivative containing a low level of substituent groups as well as cationic quaternary ammonium groups. Also suitable is Jaguar® 162 which is a high transparency, medium viscosity guar having a low degree of substitution. Especially preferred is Jaguar® C13S.

Also includable are minor amounts of other ingredients commonly found in hair care compositions, such as preservatives, keratin amino acids, UV inhibitors, fragrances, coloring agents, buffering agents, polyols and other moisturizing agents, herb extracts, mink oil or honey.

The following examples will more fully illustrate the embodiments of the present invention. All parts, percentages and proportions referred to herein and in the appended claims are by weight unless otherwise indicated.

EXAMPLES 1–5

The following transparent gel compositions are representative of the present invention.

| INGREDIENTS | EXAMPLE (WEIGHT %) | | | | |
|---|---|---|---|---|---|
| | 1 | 2 | 3 | 4 | 5 |
| PVP/VA (70/30 ratio; 50% solids) | 8.0 | — | 12.0 | 6.0 | — |
| PVP (50% solids) | — | 8.0 | — | — | 6.0 |
| Arosurf ® 66E-20 (Polyethylene glycol 20-stearyl ether) | 0.8 | 0.8 | 1.2 | 0.6 | 0.6 |
| Stabileze ® QM (Methylvinyl ether/ Maleic Anhydride Copolymer) | 0.24 | 0.24 | 0.1 | 0.50 | 0.50 |
| Fragrance | 0.1 | 0.1 | 0.1 | 0.1 | 0.1 |
| Caustic Soda | 0.07 | 0.07 | 0.07 | 0.07 | 0.07 |
| Glydant Plus ® (DMDM Hydantoin) | 0.05 | 0.05 | 0.05 | 0.05 | 0.05 |
| Crotein ® HKP (Hair Keratin Amino Acids) | 0.01 | 0.01 | 0.01 | 0.01 | 0.01 |
| Uvinul ® MS-40 (UV Inhibitor) | 0.002 | 0.002 | 0.002 | 0.002 | 0.002 |
| Phytantriol (3,7,11,15-tetramethyl-1,2,3-hexadecanetriol) | 0.001 | 0.001 | 0.001 | 0.001 | 0.001 |
| Water | balance | balance | balance | balance | balance |

EXAMPLE 6

Various surfactants were evaluated for their effect upon the gel structure of hair treatment compositions according to the present invention. A gel base essentially identical to Example 1 but absent surfactant was employed for evaluation purposes. This base contained 0.24% Stabileze® QM and 7.5% Luviskol® VA 73W (PVP/VA in 70/30 ratio).

The gel base was divided into six groups. Each was formulated with 0.8% surfactant, except for one group which was employed as a control. Among the surfactants were two anionic (ammonium lauryl sulfate and sodium lauroyl sarcosinate), one cationic (cetrimonium chloride), one amphoteric (cocamidopropyl betaine), and one nonionic (steareth-20) surfactant. Results are reported in the Table below.

| SURFACTANTS | GEL STRUCTURE | SPRAY CHARACTERISTICS | SURFACE TENSION |
|---|---|---|---|
| Ammonium Lauryl Sulfate | broke down (14 cps) | good | 35.2 dynes/cm |
| Sodium Lauroyl Sarcosinate | broke down (46 cps) | good | 31.1 dynes/cm |
| Cocamido Propyl Betaine | broke down (26 cps) | good | 31.5 dynes/cm |
| Steareth-20 | very good (14,000 cps) | very good | 42.9 dynes/cm |
| Cetrimonium Chloride | broke down | poor | — |
| No Surfactant | very good (14,000 cps) | good | 62.2 dynes/cm |

Evident from the Table is that the gel structure achieved by the combination of Stabileze® and Luviskol® VA 73W broke down in the presence of both anionic surfactants, the cationic and amphoteric surfactants. Only the nonionic surfactant retained the gel structure; it was also the only formulation that had very good spray characteristics.

EXAMPLE 7

Nozzle orifice clogging is a constant problem in pump hairstyling products, especially with relatively thick viscous formulations. Film-forming resins and thickeners tend to settle within the exit orifices. Carbomers, the thickeners most often employed in commercial hair gel spray products, have been linked to the clogging phenomena.

The following experiments were conducted to evaluate the anti-clogging effects of compositions according to the present invention. The gel product of Example 1 (with Arosurf® 66E-20) was compared to DEP® Spray Gel, a leading commercial product. Example 1 and the DEP® Spray Gel had viscosities of 11,000 cps and 8,000 to 10,000 cps, respectively. Each was divided into six separate samples. These were sprayed in 10–12 strokes daily except for weekends over a four week period.

During this time, none of the Example 1 product showed any sign of orifice clogging. By contrast, the DEP® Spray Gel had 4 partial or severe blockages. Further, it was observed that the Example 1 product was smoother, softer and had better defined spray characteristics than that of the commercial product. Since both of the products utilize the same pump mechanism, the main difference between the two is believed to be in the rheology of the gel products.

Although this invention has been described with reference to specific examples, it will be apparent to one skilled in the art that various modifications will be suggested, all of which are within the spirit and purview of this invention.

What is claimed is:

1. A hair treatment product comprising:
   (a) a pump dispenser including a spray nozzle through which a hair treatment composition is sprayed; and
   (b) a hair treatment composition contained within the dispenser comprising:
   (i) from 0.01 to 10% by weight of a crosslinked $C_1$–$C_{10}$ alkyl vinyl ether/maleic anhydride copolymer;
   (ii) from 0.1 to 20% by weight of a film-forming resin; and
   (iii) from 0.01 to 10% by weight of a nonionic surfactant which is a $C_8$–$C_{22}$ fatty alcohol ethoxylated with from 12 to 40 moles ethylene oxide.

2. The product according to claim 1 wherein the nonionic surfactant is polyethylene glycol 20-stearyl ether.

3. The product according to claim 1 wherein the copolymer is methylvinyl ether/maleic anhydride copolymer crosslinked with 1,9-decadiene.

4. The product according to claim 1 wherein the film-forming resin is selected from the group consisting of polyvinylpyrrolidone, copolymers of polyvinylpyrrolidone and methylmethacrylate, copolymers of polyvinylpyrrolidone and vinyl acetate, polyvinyl alcohol, copolymers of polyvinyl alcohol and crotonic acid, copolymers of polyvinyl alcohol and maleic anhydride, hydroxypropyl cellulose, hydroxypropyl guar gum, sodium polystyrene sulfonate, polyvinyl pyrrolidone/ethylmethacrylate/methacrylic acid terpolymer, vinyl acetate/crotonic acid/vinyl neodecanoate copolymer, octylacrylamide/acrylates copolymer and octylacrylamide/acrylate/butylaminoethyl methacrylate copolymers and mixtures thereof.

5. The product according to claim 1 wherein the water soluble film-forming resin is polyvinylpyrrolidone/vinyl acetate.

6. The product according to claim 1 further comprising from 0.0001 to 1% phytantriol.

* * * * *